United States Patent [19]
Chen et al.

[11] Patent Number: 6,113,938
[45] Date of Patent: Sep. 5, 2000

[54] BENEFICIAL AGENT DELIVERY SYSTEM WITH MEMBRANE PLUG AND METHOD FOR CONTROLLING DELIVERY OF BENEFICIAL AGENTS

[75] Inventors: Guohua Chen, Sunnyvale; Scott Lautenbach, San Mateo, both of Calif.; Keith Dionne, Cambridge, Mass.; Lawton Hom, San Francisco, Calif.

[73] Assignee: ALZA Corporation, Mountain View, Calif.

[21] Appl. No.: 09/121,835

[22] Filed: Jul. 24, 1998

Related U.S. Application Data

[60] Provisional application No. 60/070,011, Dec. 30, 1997.

[51] Int. Cl.[7] ............................................. A61F 2/02
[52] U.S. Cl. ............................................. 424/423
[58] Field of Search ............................................. 424/423

[56] References Cited

U.S. PATENT DOCUMENTS

| | | | |
|---|---|---|---|
| 3,732,865 | 5/1973 | Higuchi et al. | 128/260 |
| 3,995,631 | 12/1976 | Higuchi et al. | 128/260 |
| 3,995,632 | 12/1976 | Nakano et al. | 128/260 |
| 4,111,202 | 9/1978 | Theeuwes | 128/260 |
| 4,243,030 | 1/1981 | Lynch et al. | 128/213 |
| 4,340,054 | 7/1982 | Michaels | 128/260 |
| 4,373,527 | 2/1983 | Fischell | 128/260 |
| 4,439,196 | 3/1984 | Higuchi | 604/890 |
| 4,552,561 | 11/1985 | Eckenhoff et al. | 604/896 |
| 4,639,244 | 1/1987 | Rizk et al. | 604/19 |
| 4,865,845 | 9/1989 | Eckenhoff et al. | 424/424 |
| 4,874,388 | 10/1989 | Wong et al. | 424/438 |
| 5,137,727 | 8/1992 | Eckenhoff | 424/422 |
| 5,223,265 | 6/1993 | Wong | 424/473 |
| 5,279,608 | 1/1994 | Cherif Cheikh | 604/892.1 |
| 5,308,348 | 5/1994 | Balaban et al. | 604/892 |
| 5,312,389 | 5/1994 | Theeuwes et al. | 604/892.1 |
| 5,312,390 | 5/1994 | Wong | 604/892.1 |
| 5,456,679 | 10/1995 | Balaban et al. | 604/892.1 |
| 5,728,396 | 3/1998 | Peery et al. | 424/422 |

*Primary Examiner*—Carlos A. Azpuru
*Attorney, Agent, or Firm*—Cindy A. Lynch; Steven F. Stone; Pauline A. Clarke

[57] ABSTRACT

An osmotic delivery system for controlled delivery of a beneficial agent includes an implant capsule containing a beneficial agent and an osmotic agent which swells on contact with water causing the release of the beneficial agent over time. The osmotic delivery system has a membrane plug which allows water to pass through the plug from an exterior of the capsule while preventing the compositions within the capsule from passing out of the capsule. A delivery rate for delivery of the beneficial agent from the implant capsule is controlled by varying a core diameter of the membrane plug within a constant diameter capsule. The membrane plug has a variable water permeation rate depending on an extent to which the membrane plug is constrained by the capsule walls.

16 Claims, 7 Drawing Sheets

BENEFICIAL AGENT DELIVERY SYSTEM WITH MEMBRANE PLUG AND METHOD FOR CONTROLLING DELIVERY OF BENEFICIAL AGENTS

This application claims the benefit of U.S. Provisional No. 60/070,011 filed Dec. 30, 1997.

BACKGROUND OF THE INVENTION

1. Field of the Invention

The present invention relates to osmotic and diffusion controlled implantable delivery devices, and more particularly, to a delivery system with a membrane plug which controls the delivery rate of a beneficial agent from the delivery system.

2. Description of the Related Art

Controlled delivery of beneficial agents, such as drugs, in the medical and the veterinary fields has been accomplished by a variety of methods, including implantable delivery devices such as implantable osmotic delivery systems and implantable diffusion controlled delivery systems. Osmotic delivery systems are very reliable in delivering a beneficial agent over an extended period of time called an administration period. In general osmotic delivery systems operate by imbibing fluid from an outside environment and releasing corresponding amounts of a beneficial agent from the delivery system.

Osmotic delivery systems, commonly referred to as "osmotic pumps," generally include some type of capsule having walls which selectively pass water into the interior of the capsule containing a water attracting agent. The absorption of water by the water attracting agent within the capsule reservoir creates an osmotic pressure within the capsule which causes a beneficial agent within the capsule to be delivered. The water attracting agent may be the beneficial agent being delivered to the patient, however, in most cases, a separate agent is used specifically for its ability to draw water into the capsule.

When a separate osmotic agent is used, the osmotic agent may be separated from the beneficial agent within the capsule by a movable dividing ember or piston. The structure of the capsule is generally rigid such that as the osmotic agent takes in water and expands, the capsule does not expand. As the osmotic agent expands, the agent causes the movable dividing member or piston to move discharging the beneficial agent through an orifice or exit passage of the capsule. The beneficial agent is discharged through the exit passage at the same volumetric rate that water enters the osmotic agent through the semipermeable walls of the capsule.

The rate at which the beneficial agent is discharged from the delivery device is determined by many factors including the type of osmotic agent, the permeability of the semipermeable membrane walls, and the size and shape of the exit passage. One manner in which the delivery rate of the beneficial agent is controlled is by a flow moderator in the exit passage of the capsule which generally consist of a tubular passage having a particular cross sectional area and length.

In the known osmotic delivery systems, an osmotic tablet such as salt is placed inside the capsule and a membrane plug is placed in an open end of the capsule to provide a semipermeable wall. The membrane plug seals the interior of the capsule from the exterior environment permitting only certain liquid molecules from the environment to permeate through the membrane plug into the interior of the capsule. The membrane plug is impermeable to items within the capsule including the osmotic agent and the beneficial agent. The rate at which liquid permeates the membrane plug and enters the capsule varies depending upon the type of membrane material and the size and shape of the membrane plug. The rate at which the liquid passes through the membrane plug controls the rate at which the osmotic agent expands driving the beneficial agent from the delivery system through the exit passage. Accordingly, the rate of delivery of the beneficial agent from the osmotic delivery system is controllable by varying the permeability coefficient of the membrane plug or the size of the membrane plug.

Osmotic delivery systems requiring a high beneficial agent delivery rate typically use membrane plugs having high permeability coefficients while systems requiring low beneficial agent delivery rate use membrane plugs having a low permeability coefficient. Thus, the delivery rate of the beneficial agent in a known osmotic delivery system may be varied by forming a membrane plug having the same size and shape from different semipermeable materials. The use of a different membrane material for each system in which a different beneficial agent delivery rate is desired requires the development and manufacture of many different membrane materials and the manufacture of many different membrane plugs.

Some types of membrane plugs can swell and expand significantly when wetted. This ability to swell provides a self-sealing function between the membrane plug and the capsule walls and prevents the need for an adhesive to retain the membrane plug inside the capsule. When the membrane plug is inserted in an open end of a rigid capsule, the space for the membrane plug to swell and expand is limited by the capsule walls, thus, the membrane plug will sometimes be performing in a constrained condition. This constraint of the membrane plug causes a change in the membrane performance over time. For example, as the membrane plug becomes constrained due to swelling the morphology of the membrane material changes resulting from cold creep. This causes the beneficial agent delivery rate to change over time.

Due to the above-identified problem associated with the current osmotic delivery systems, it is costly and particularly difficult to administer beneficial agents from an osmotic delivery system at different desired delivery rates with the same system. A different membrane plug material must be selected for each application depending on the beneficial agent delivery rate desired.

SUMMARY OF THE INVENTION

In accordance with the present invention, a delivery system for controlled delivery of a beneficial agent includes an implantable capsule having an opening, a beneficial agent reservoir within the capsule for delivery of the beneficial agent at a predetermined delivery rate, and a membrane plug received in the opening of the capsule. The membrane plug provides a fluid permeable barrier between an interior and an exterior of the capsule. The membrane plug has a plurality of external ribs for engaging an interior surface of the capsule and a clearance between exterior surfaces of the membrane plug and the interior surfaces of the capsule is preselected to achieve the predetermined delivery rate at which the beneficial agent is delivered from the reservoir.

In accordance with another aspect of the present invention, a method of forming a beneficial agent delivery device includes the steps of filling a chamber of a delivery device capsule with a beneficial agent, selecting a delivery rate for delivery of the beneficial agent from the chamber of the delivery device capsule, and selecting a membrane plug having a plurality of retention ribs and a core diameter between the ribs. A clearance between the membrane plug and an interior surface of the delivery device capsule is selected to achieve the predetermined delivery rate for delivery of the beneficial agent. The open end of the chamber is plugged with the selected membrane plug.

According to a further aspect of the invention, a method of making an osmotic delivery device for the delivery of beneficial agents includes the steps of filling a reservoir in a body with a beneficial agent and an osmotic agent, providing a membrane plug for sealing an opening in the body, the membrane plug formed of a material which allows aqueous fluids to pass through the membrane into the osmotic agent and prevents the osmotic agent from passing out of the body, and compensating for variations in raw materials used for the membrane plug by varying a clearance between the membrane plug and an interior of the body.

In accordance with an additional aspect of the present invention, a method of controlling a release rate of an osmotic delivery device for delivery of beneficial agents includes providing a delivery device body with a reservoir containing a beneficial agent, a beneficial agent delivery outlet through which the beneficial agent is released, an osmotic agent, and a membrane plug positioned between the osmotic agent and an exterior of the body, the membrane plug allowing aqueous fluid to pass into the reservoir to swell the osmotic agent while preventing fluid from passing out of the body through the membrane plug, the membrane plug having a diameter which fits into an end of the reservoir. The release rate of the beneficial agent from the body is controlled by selecting a clearance between the membrane plug and an interior of the body such that a release rate of a delivery device with a smaller clearance is lower than a release rate of a delivery device with a larger clearance.

The present invention provides the advantage of a more controllable beneficial agent delivery rate by preventing constraint of a membrane plug.

The present invention also provides an advantage of allowing control of a beneficial agent delivery rate without changing a shape of an implant capsule or a material of a membrane plug.

In addition, the present invention allows the control of a beneficial agent delivery rate by changing a membrane shape or an implant capsule shape.

BRIEF DESCRIPTION OF THE DRAWINGS

The invention will be described in greater detail with reference to the accompanying drawings in which like elements bear like reference numerals, and wherein.

DESCRIPTION OF THE PREFERRED EMBODIMENTS

Figure 1:
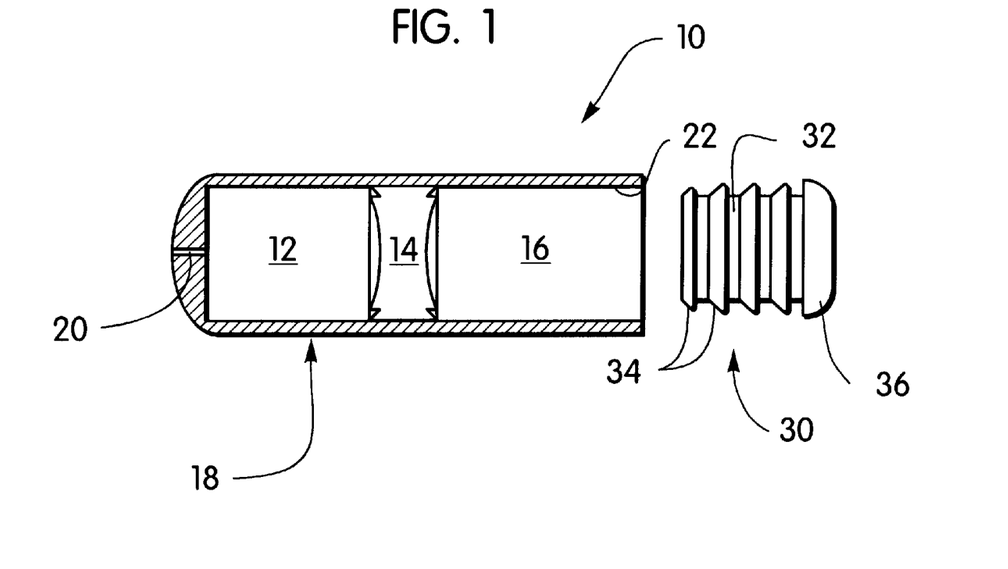
FIG. 1 is an exploded cross-sectional view of an osmotic drug delivery device.

The present invention relates to an osmotic delivery system having a membrane plug 30 for controlling a delivery rate of a beneficial agent from the osmotic delivery system. FIG. 1 shows the osmotic delivery device 10 generally including a first chamber 12 containing a beneficial agent, a piston 14 and a second chamber 16 containing an osmotic agent, all of which are enclosed within an elongated substantially cylindrical capsule 18. The capsule 18 has an exit passage 20 at a first end of the capsule and an open end 22 at the second end of the capsule. The capsule 18 is preferably formed of a relatively rigid material which withstands expansion of the osmotic agent without changing in size or shape.

The open end 22 in the capsule 18 is closed by the membrane plug 30 which is illustrated in FIG. 1 in an orientation in which it is inserted into the opening. The membrane plug 30 closes the open end 22 of the second chamber 16 containing the osmotic agent. The osmotic agent may be, for example, a nonvolatile water soluble osmagent, an osmopolymer which swells on contact with water, or a mixture of the two. The membrane plug 30 allows water to pass through the plug from an exterior of the capsule 18 into the second chamber 16 while preventing the compositions within the capsule from passing out of the capsule through the membrane plug.

The first chamber 12 containing the beneficial agent is separated from the second chamber 16 containing the osmotic agent by a separating member, such as the movable piston 14. The piston 14 is a substantially cylindrical member which is configured to fit within the interior diameter of the capsule 18 in a sealing manner and to slide along a longitudinal axis of the capsule. The piston 14 provides an impermeable barrier between the beneficial agent of the first chamber 12 and the osmotic agent of the second chamber 16.

In accordance with the present invention, a clearance between the membrane plug 30 and the inner diameter of the capsule 18 is selected to achieve a predetermined delivery rate of the beneficial agent from the delivery device. By changing the membrane plug clearance, a rate at which liquid permeates the membrane plug is altered based on an amount the membrane material is constrained by the capsule side walls. The constrained condition of the membrane plug will be described in further detail below.

Figure 2:
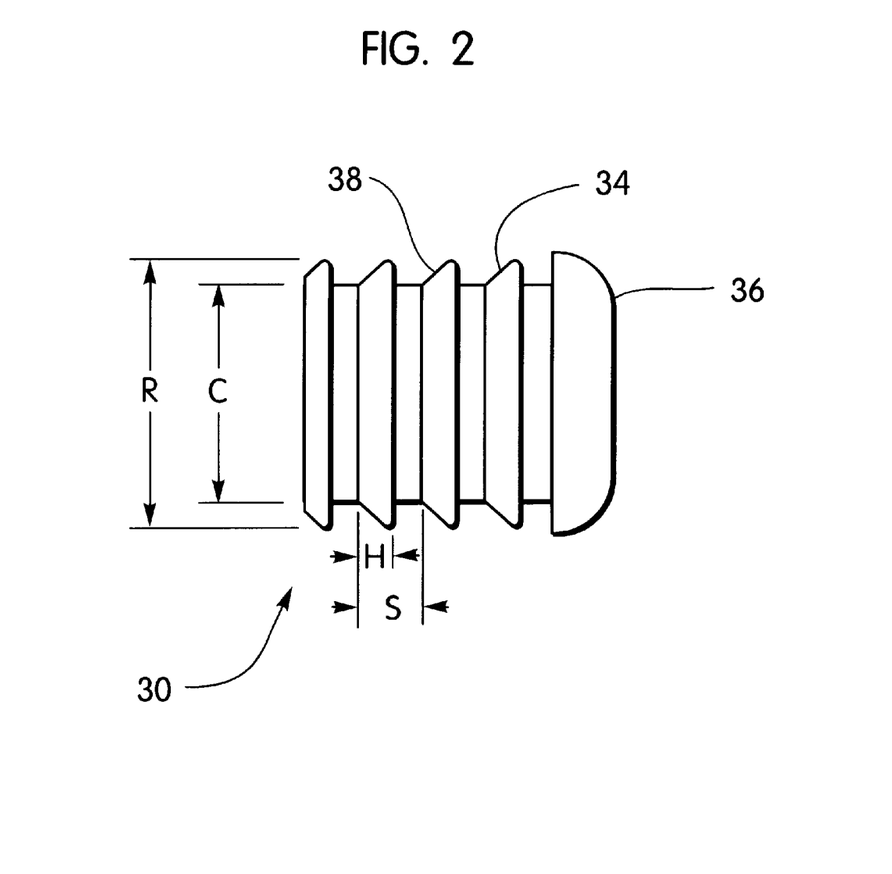
FIG. 2 is a side elevational view of a membrane plug according to one embodiment of the present invention.

The membrane plug 30, as shown in FIG. 2, includes a substantially cylindrical body 32, having a plurality of ribs 34 and an enlarged end cap 36 positioned on one end of the cylindrical body. The ribs 34 extend from the cylindrical body 32 and provide means for sealing between the outer surface of the membrane plug 30 and the interior walls of the capsule 18. The ribs 34 have an angled forward surface 38 which helps in insertion of the membrane plug 30 into the capsule and prevents membrane plug expulsion. Although the ribs 34 have been illustrated as continuous annular ribs, the ribs may also be formed in other shapes such as threads, interrupted ribs, ridges, or the like.

Upon insertion of the membrane plug 30 into the open end 22 of the capsule 18, the end cap 36 acts as a stop member engaging an end of the capsule and achieving a repeatable position of the membrane plug inside the capsule. The end cap 36 also provides additional sealing. The membrane plug 30 is illustrated as including an end cap 36 which provides a stop surface to provide a uniform insertion distance of the membrane plug into the capsule 18. Alternatively, the plug may be provided without an end cap and the plug may be inserted entirely within the open end 22 of the capsule 18.

As mentioned above, the membrane plug 30 is made from a semipermeable material which allows liquids, especially water, to pass from an exterior environment into the capsule 18 to cause the osmotic agent within the second chamber 16 to swell. The semipermeable material of the membrane plug 30 is largely impermeable to the materials contained within the capsule 18. Semipermeable compositions suitable for the membrane plug 30 are known in the art, examples of these compositions are disclosed in U.S. Pat. No. 4,874,388, the entire disclosure of which is incorporated herein by reference.

The semipermeable material of the membrane plug 30, once inserted into the open end of the capsule 18, will expand significantly when wetted depending on the membrane material. An unconstrained membrane plug expands between 5 and 50 percent when wetted depending on the membrane material. This expansion of the membrane plug 30 when wetted improves the sealing characteristics between the membrane plug ribs 34 and the interior capsule walls. However, with a rigid capsule 18 the expansion space for the membrane plug 30 to swell is limited by the walls of the capsule. This limited expansion causes a so called constrained condition of the membrane plug. With time the constrained condition causes cold creep of the material of the membrane plug. The cold creep causes the membrane plug 30 to change morphology leading to a change in water permeation rate over time. The change of the membrane plug 30 permeability over time results in a corresponding change in the release rate of the beneficial agent from the osmotic delivery system.

In order to address the changing water permeation rate of the membrane plug 30 over time, a clearance between the membrane plug and the capsule walls is selected to achieve the desired delivery rate. The change in the clearance may be accomplished by changing either a configuration of the membrane plug or a configuration of the capsule. As will be described in further detail below, it is generally easier to change the shape of the membrane rather than changing the capsule because the membrane plug may be changed without requiring changes to other components of the delivery device 10, such as the piston 14.

FIG. 2 illustrates a membrane plug 30 having a core diameter C between the ribs 34 and a rib diameter R of the ribs. Each of the ribs 34 has a rib height H and a rib segment height S which encompasses both the rib and the space between one rib and the next. For a predetermined capsule inner diameter, the clearance is changed by changing different dimensions of the membrane such as the core diameter C, the rib diameter R, or the rib height H. The core diameter C of the membrane plug is preferably between 0.5 and 15 percent smaller that the interior diameter of the capsule. However, a change in any one of the dimensions of the membrane plug discussed above effects the clearance and, thus, changes the delivery rate of the beneficial agent.

In accordance with one embodiment of the present invention, a desired delivery rate for an osmotic delivery device can be achieved without varying the physical configuration of the delivery capsule 18 or the material of the membrane plug 30. A plurality of membrane plugs 30 may be provided each having 1) the same rib diameter and a different core diameter; 2) the same core diameter and different rib diameters; or 3) different rib heights for a constant rib segment height S. A membrane plug is selected from the plurality of different plugs which are available to achieve a desired delivery rate based on the clearance. This procedure of providing osmotic delivery systems with a plurality of different drug delivery rates by changing the configuration of the membrane plug will allow different delivery rates to be achieved without changing the configuration of the capsule 18 or the material of the membrane plug 30.

Figure 3:
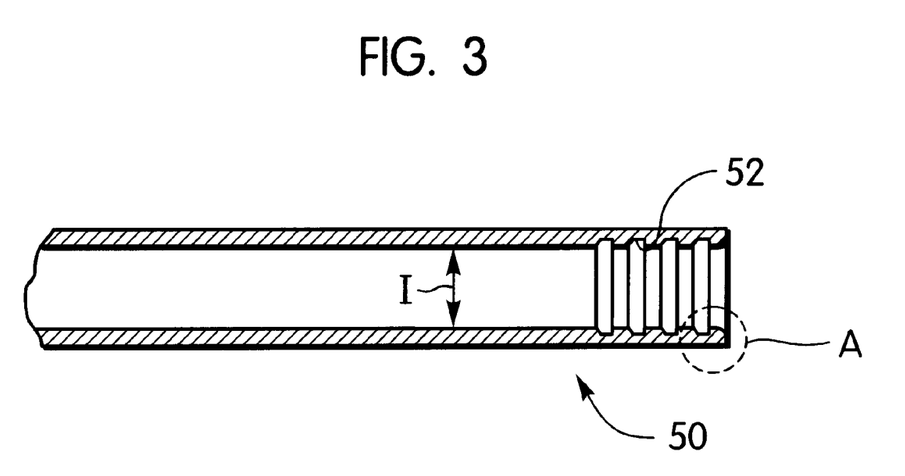
FIG. 3 is a side cross-sectional view of a portion of an implant capsule according to a second embodiment of the invention.
Figure 4:
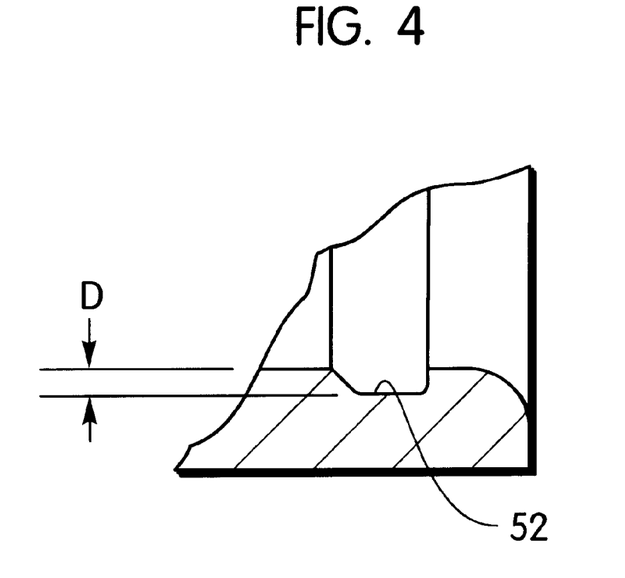
FIG. 4 is an enlarged view of the detail A of FIG. 3.

FIG. 3 shows an alternative embodiment of a capsule 50 having a plurality of grooves 52 for receiving the ribs 34. An enlarged view of the detail A is shown in FIG. 4 in which a groove 52 has a groove depth D. Variation of the groove depth D for a predetermined membrane plug configuration will change the clearance and, thus the delivery rate. Further, variation of the capsule inner diameter I for a predetermined membrane plug configuration will also change the clearance and the delivery rate.

As described above, the clearance or the space between the membrane plug and the capsule may be modified by changing different dimensions of either the membrane plug 30 or the capsule 18. The dimensions which have been discussed above are merely examples. It should be understood that other dimensions can also be changed to change the clearance, such as the angle of the inclined surfaces 38 of the ribs.

The term clearance is intended to include both positive clearances where there is space between the membrane plug 30 and the capsule 18 and negative clearances, or interferences, between the membrane plug and the capsule. The rib interference between any rib 34 and corresponding groove 52 preferably ranges from −1% to 8% of the inside diameter of the groove, i.e., the rib preferably has a diameter from about 1% smaller to about 8% larger than the inner diameter of the capsule groove.

In addition to allowing modification of a delivery rate by changing the clearance, the present invention allows compensation for lot to lot variation in the raw materials of the membrane plug 30. In particular, it is difficult to obtain raw membrane materials having identical or substantially identical liquid permeation rates between different material lots. Accordingly, it is possible to manufacture a plurality of osmotic delivery systems having very consistent drug delivery rates with the slight variation between membrane material lots compensated for by varying the clearance between the membrane plug and the capsule.

Figure 5:
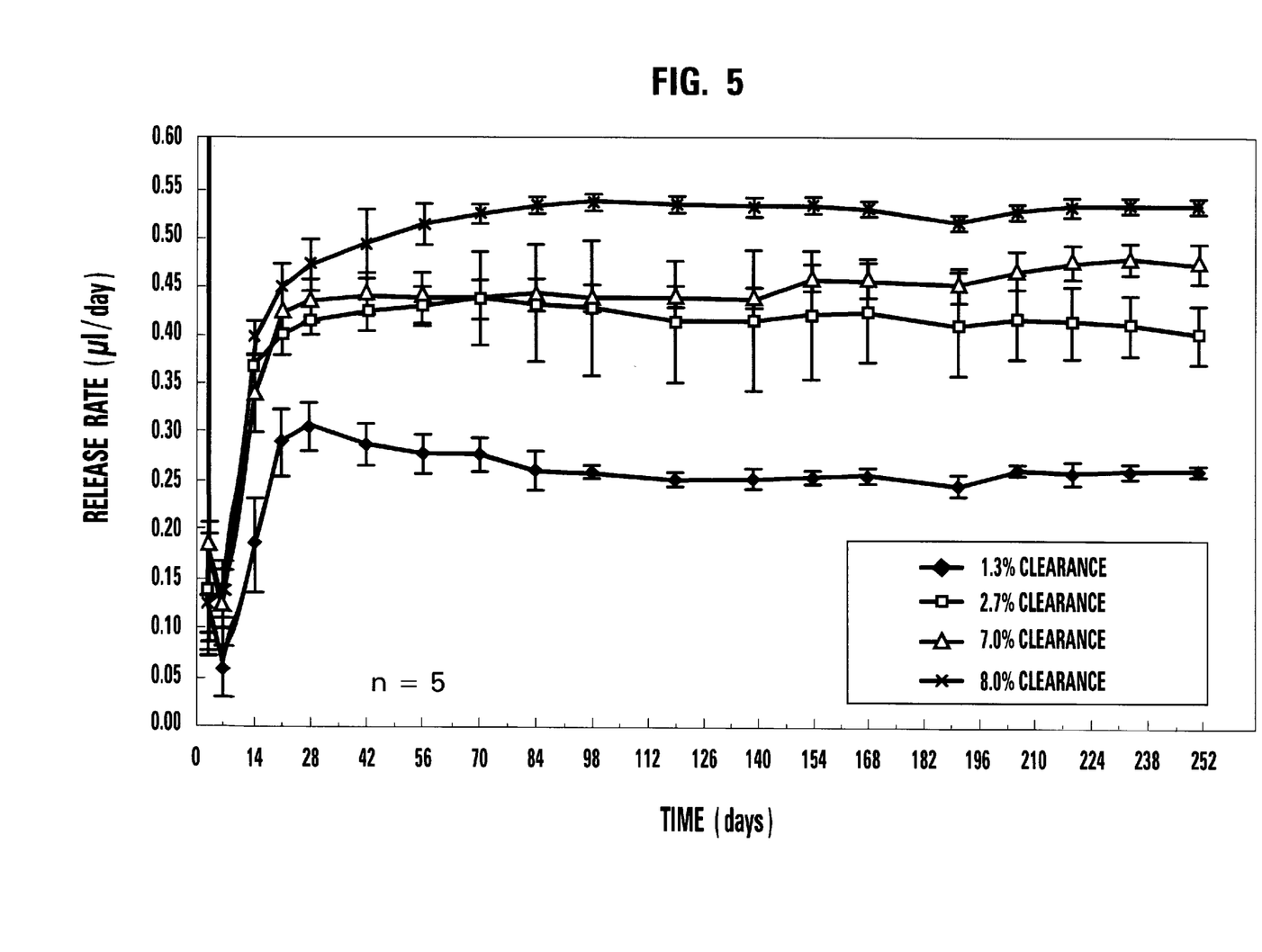
FIG. 5 is a graph of the effect of small changes in membrane plug core diameter on a delivery fluid release rate for a first membrane material.

FIG. 5 is a graph illustrating the effect of small changes in membrane plug core diameter C on the release rate of a fluid over a 252-day administration period. For this example, four membranes having different core diameters C (1.3%, 2.7%, 7.0%, and 8.0% clearance) and a constant rib diameter R were inserted into delivery device capsules having osmotic agents and pistons and with a dye in place of the beneficial agent. The four membrane plugs were formed of polyurethane Tecophilic (HP-60D-20). The membrane core diameter C is represented by a percent clearance, such that a 1.3% clearance membrane plug has a core diameter which is 1.3% of an inner diameter of the capsule and a 2.7% clearance membrane plug has a core diameter which is 2.7% of the inner diameter of the capsule.

As shown in FIG. 5, the release rate for the delivery system with a membrane plug having a 1.3% clearance decreased over the 252-day administration period by about 0.05 μl/day, due to the constrained condition of the membrane plug material and the changing morphology of the plug. In contrast, the implant systems having membrane plugs with 2.7%, 7.0%, and 8.0% clearances achieve successively higher and substantially constant release rates over the administration period after the initial startup period.

Figure 6:
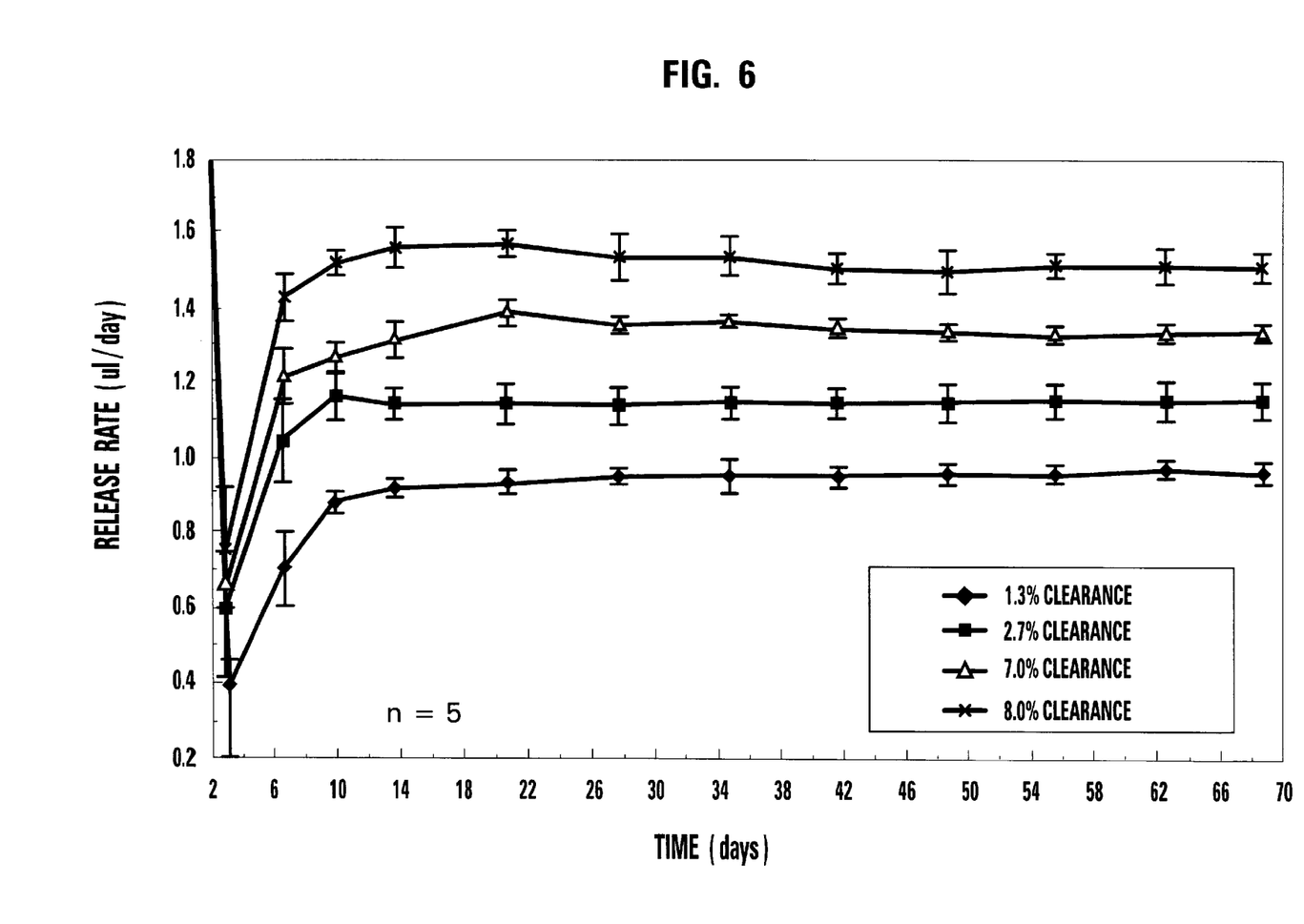
FIG. 6 is a graph of the effect of small changes in membrane plug core diameter on a delivery fluid release rate for a second membrane material.
Figure 7:
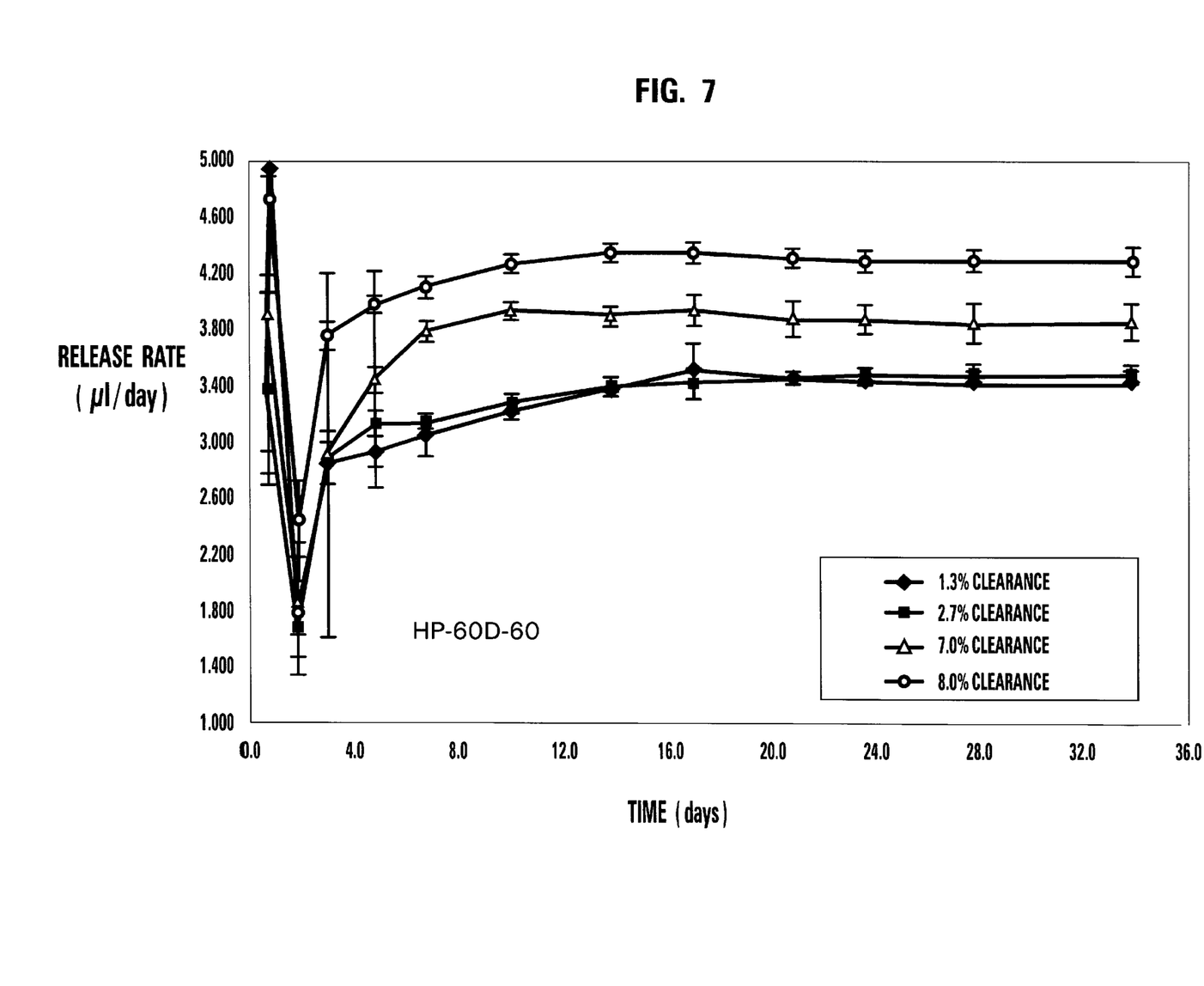
FIG. 7 is a graph of the effect of small changes in membrane plug core diameter on a delivery fluid release rate for a third membrane material.

FIGS. 6 and 7 illustrate the results of an experiment similar to that of FIG. 5 except that a different membrane material has been used. The membranes used in the experiments recorded in FIGS. 6 and 7 are formed of Tecophilic (HP60D-35) and Tecophilic (HP-60D-60), respectively. The release rates of these systems experience minimal change over the administration period after an initial startup period. However, these types of membrane materials achieved substantially different delivery rates depending on the membrane plug core diameter C. Accordingly, the membrane material can be used to achieve different delivery rates by changing the membrane plug core diameter C without otherwise altering the implant system. It is noted that the Tecophilic (HP-60D-60) had little change in release rate between 1.3% and 2.7% clearance indicating that larger clearances are needed to achieve a change in release rate for this material.

Figure 8:
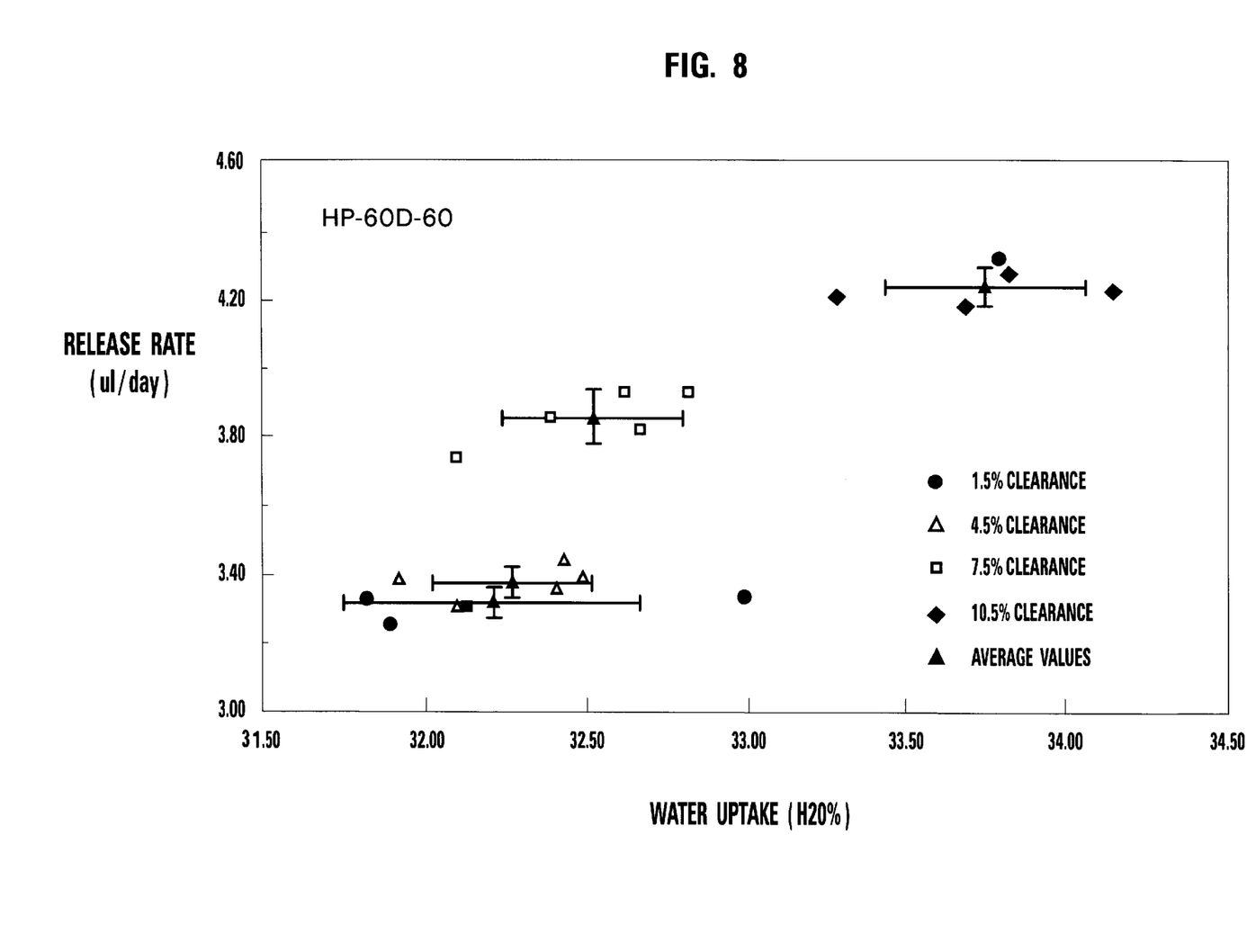
FIG. 8 is a graph of the effect of small changes in membrane plug core diameter on the release rate and water uptake rate.

FIG. 8 illustrates the correlation of the release rate with the water uptake of the membrane for membrane plugs having a core diameter C of the membrane plug which is 1.5%, 4.5%, 7.5%, and 10.5% less than the implant capsule inner diameter. The membrane material of FIG. 8 is the same material (HP-60D-60) as the material in FIG. 7. As shown in FIG. 8, the release rate is proportional to the water uptake rate of the membrane with larger clearances providing both a greater water uptake and a higher beneficial agent release rate.

In FIGS. 5–8 the core diameter C of the membrane plug is changed to change the clearance while other dimensions of the membrane plug 30 and the capsule 18 remain constant. It should be understood that a similar effect on the release rate can be achieved by changing the inner diameter I of the capsule to change the clearance, or by changing the rib diameter R or the rib height H.

Figure 9:
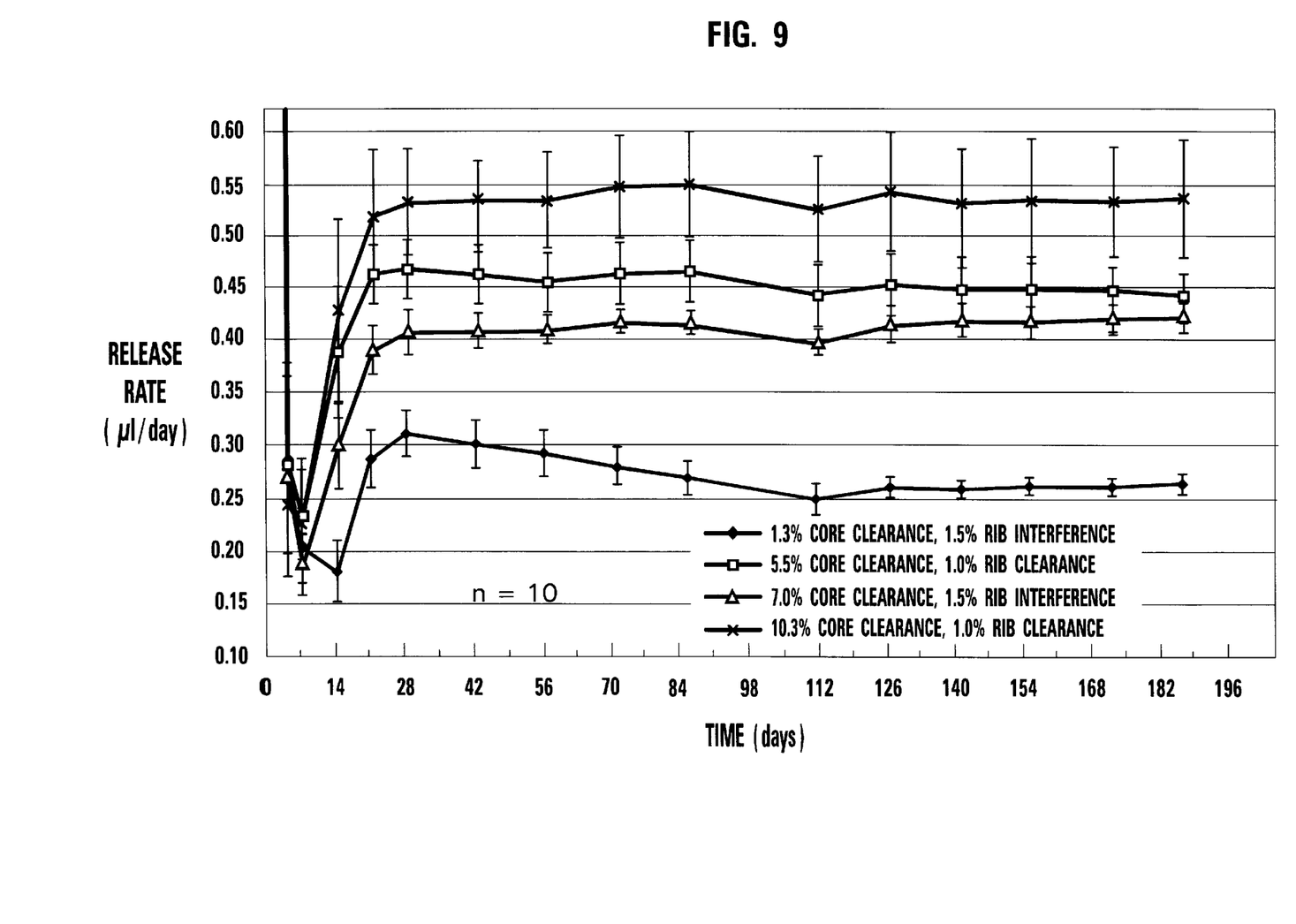
FIG. 9 is a graph of the effect of small changes in core diameter and rib diameter on a delivery fluid release rate for the first membrane material.

FIG. 9 illustrates the change in release rate when both the core diameter C and the rib diameter R of the membrane plug are changed. The membrane material used in the example of FIG. 9 is the same material used in the example of FIG. 5 (HP-60D-20). However, in FIG. 9, the rib diameter R was varied from a 1.0% clearance to a −1.5% clearance (1.5% interference). When the rib diameter R was increased in the 7.0% core clearance, 1.5% rib interference membrane this caused the total clearance to decrease resulting in a decrease in the release rate, as shown by the fact that the 7.0% core clearance line is below the 5.5% core clearance line. Accordingly, although the change in the clearance has been illustrated by changing one or two dimensions of the delivery system, the clearance may be changed by varying any one or more of the dimensions effecting clearance.

Examples of semipermeable materials for the membrane plug 30 include, but are not limited to, polyurethane, polyetherblockamide (PEBAX, commercially available from ELF ATOCHEM, Inc.), injection-moldable thermoplastic polymers with some hydrophilicity such as ethylene vinyl alcohol (EVA), and hydrophilic acrylate polymers, such as hydroxyethyl methacrylate (HEMA). In general, the membrane plug 30 is made from semipermeable materials having a water uptake ranging from 1% to 80%, and preferably less than 50%. The composition of the semipermeable membrane plug 30 is permeable to the passage of external liquids such as water and biological liquids, and it is substantially impermeable to the passage of beneficial agents, osmopolymers, osmagents, and the like.

Other materials for the membrane plug 30 are hytrel polyester elastomers (DuPont), cellulose esters, cellulose ethers and cellulose ester-ethers, water flux enhanced ethylene-vinyl acetate copolymers, semipermeable membranes made by blending a rigid polymer with water-soluble low molecular weight compounds, and other semipermeable materials well known in the art. The above cellulosic polymers have a degree of substitution, D.S., on the anhydroglucose unit, from greater than 0 up to 3 inclusive. "Degree of substitution" or "D.S." means the average number of hydroxyl groups originally present on the anhydroglucose unit comprising the cellulose polymer that are replaced by a substituting group. Representative materials include, but are not limited to, one selected from the group consisting of cellulose acylate, cellulose diacylate, cellulose triacylate, cellulose acetate, cellulose diacetate, cellulose triacetate, mono-, di-, and tricellulose alkanylates, mono-, di-, and tricellulose aroylates, and the like. Exemplary cellulosic polymers include cellulose acetate having a D. S. up to 1 and an acetyl content up to 21%; cellulose acetate having a D. S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose acetate butyrate having a D S. of 1.8, and acetyl content of 4% average weight percent and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like.

Materials which may be used for the capsule 18 should be sufficiently strong to ensure that the capsule will not leak, crack, break, or distort under stresses to which they would be subjected during implantation or under stresses due to the pressures generated during operation. The capsule may be formed of chemically inert and biocompatible, natural or synthetic materials which are known in the art. The material of the capsule is preferably a non-bioerodible material which remains in the patient after use, such as titanium. However, the material of the capsule may alternatively be of bioerodible material which bioerodes in the environment after dispensing of the beneficial agent. Generally, preferred materials for the capsule are those acceptable for human implants.

In general, typical materials of construction suitable for the capsule according to the present invention include non-reactive polymers or biocompatible metals or alloys. The polymers include acrylonitrile polymers such as acrylonitrile-butadiene-styrene terpolymer, and the like; halogenated polymers such as polytetraflouroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Metallic materials useful for the capsule include stainless steel, titanium, platinum, tantalum, gold, and their alloys, as well as gold-plated ferrous alloys, platinum-plated ferrous alloys, cobalt-chromium alloys and titanium nitride coated stainless steel.

In general, materials suitable for use in the piston are elastomeric materials including the non-reactive polymers listed above, as well as elastomers in general, such as polyurethanes and polyamides, chlorinated rubbers, styrene-butadiene rubbers, and chloroprene rubbers.

The osmotic tablet is an osmotic agent which is a fluid-attracting agent used to drive the flow of the beneficial agent. The osmotic agent may be an osmagent, an osmopolymer, or a mixture of the two. Species which fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite polyacrylic acids having molecular weights of 80,000 to 200,000, Polyox polyethylene oxide polymers having molecular weights of 100,000 to 5,000,000, starch graft copolymers, and Aqua-Keeps acrylate polymer polysaccharides.

Although the present invention has been described with respect to an osmotic system having as osmotic agent and a beneficial agent, it should be understood that the osmotic agent may be incorporated into the beneficial agent. In addition, the membrane plug, according to the present invention, may also be used for diffusional implantable delivery systems in which case the osmotic agent is eliminated entirely.

In one embodiment of the invention, the beneficial agents contained in the first chamber 12 are flowable compositions such as liquids, suspension, slurries, pastes, or powders and are poured into the capsule after the osmotic agent and the piston 14 have been inserted. Alternatively, such flowable compositions may be injected with a needle through a slit in a delivery port plug, which allows for filling without air bubbles. Still further alternatives may include any of the wide variety of techniques known in the art for forming capsules used in the pharmaceutical industry.

Animals to whom drugs may be administered using systems of this invention include humans and other animals. The invention is of particular interest for application to humans and household, sport, and farm animals, particularly mammals. For the administration of beneficial agents to animals, the devices of the present invention may be implanted subcutaneously or intraperitoneally or at any other location in a biological environment where aqueous body fluids are available to activate the osmotic engine.

The devices of this invention are also useful in environments outside of physiological or aqueous environments. For example, the devices may be used in intravenous systems (attached to an IV pump or bag or to an IV bottle, for example) for delivering beneficial agents to animals, primarily to humans. They may also be utilized in blood oxygenators, kidney dialysis and electrophoresis, for example. Additionally, devices of the present invention may be used in the biotechnology area, such as to deliver nutrients or growth regulating compounds to cell cultures.

The present invention applies to the administration of beneficial agents in general, which include any physiologically or pharmacologically active substance. The beneficial agent may be any of the agents which are known to be delivered to the body of a human or an animal such as drug agents, medicaments, vitamins, nutrients, or the like. The beneficial agent may also be an agent which is delivered to other types of aqueous environments such as pools, tanks, reservoirs, and the like. Included among the types of agents which meet this description are biocides, sterilization agents, nutrients, vitamins, food supplements, sex sterilants, fertility inhibitors, and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs, and synthetic analogs of these species.

Examples of drugs which may be delivered by devices according to this invention include, but are not limited to prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagultion factors, human pancreas hormone releasing factor, analogs and derivatives of these compounds, and pharmaceutically acceptable salts of these compounds, or their analogs or derivatives.

The beneficial agent can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations may be used. Derivatives such as esters, ethers and amides can also be used. An active agent can be used alone or mixed with other active agents.

According to other embodiments of the present invention, the delivery device may take different forms. For example, the piston may be replaced with a flexible member such as a diaphragm, partition, pad, flat sheet, spheroid, or rigid metal alloy, and may be made of any number of inert materials. Furthermore, the osmotic device may function without the piston, having simply an interface between the osmotic agent/fluid additive and the beneficial agent or having the osmotic agent incorporated in the beneficial agent.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

We claim:

1. A delivery system for controlled delivery of a beneficial agent at a predetermined delivery rate comprising:

an implantable capsule having an opening;

a beneficial agent reservoir within the capsule for containing the beneficial agent;

a membrane plug received in the opening of the capsule and providing a fluid permeable barrier between an interior and an exterior of the capsule, the membrane plug having a plurality of external ribs for engaging an interior surface of the capsule; and a clearance between exterior surfaces of the membrane plug and the interior surfaces of the capsule, wherein the predetermined delivery rate at which the beneficial agent is delivered from the reservoir is achieved by selecting the clearance, wherein the clearance is a difference between an exterior diameter of the external ribs and an interior diameter of the capsule, and the external ribs are between about −1% and about 8% larger than an interior diameter of grooves in the capsule.

2. The delivery system according to claim 1, wherein the clearance is a difference between an exterior diameter of the membrane plug between the ribs and an interior diameter of the capsule.

3. A delivery system for controlled delivery of a beneficial agent comprising:

an implantable capsule having an opening;

a beneficial agent reservoir within the capsule for delivery of the beneficial agent at a predetermined delivery rate;

a membrane plug received in the opening of the capsule and providing a fluid permeable barrier between an interior and an exterior of the capsule, the membrane plug having a plurality of external ribs for engaging an interior surface of the capsule;

a clearance between exterior surfaces of the membrane plug and the interior surfaces of the capsule preselected to achieve the predetermined delivery rate at which the beneficial agent is delivered from the reservoir; and wherein the diameter of the membrane plug between the ribs is between 0.5 and 15 percent smaller than the interior diameter of the capsule.

4. The delivery system according to claim 1, wherein the clearance is preselected by selecting a height of the ribs in a direction parallel to a longitudinal axis of the delivery system.

5. The delivery system according to claim 1, wherein a largest diameter of the plurality of ribs is greater than an interior diameter of the cylindrical opening of the capsule.

6. A delivery system for controlling delivery of a beneficial agent comprising:

an implantable capsule having an opening;

a beneficial agent reservoir within the capsule for delivery of the beneficial agent at a predetermined delivery rate;

a membrane plug received in the opening of the capsule and providing a fluid permeable barrier between an interior and an exterior of the capsule, the membrane plug having a plurality of external ribs for engaging an interior surface of the capsule;

a clearance between exterior surfaces of the membrane plug and the interior surfaces of the capsule preselected to achieve the predetermined delivery rate at which the beneficial agent is delivered from the reservoir; and wherein the plurality of ribs are annular ribs each having a tapered leading edge in a direction of insertion of the membrane plug.

7. The delivery system according to claim 1, wherein a core of the membrane plug between the plurality of ribs is generally cylindrical in shape.

8. The delivery system according to claim 1, further comprising a movable piston positioned within the implant capsule and separating the beneficial agent reservoir from an osmotic agent reservoir.

9. A method of forming a beneficial agent delivery device comprising:

filling a chamber of a delivery device capsule with a beneficial agent;

selecting a delivery rate for delivery of the beneficial agent from the chamber of the delivery device capsule;

selecting a membrane plug having a plurality of retention ribs and a core diameter between the ribs, wherein a clearance between the membrane plug and an interior surface of the delivery device capsule is selected to achieve the predetermined delivery rate for delivery of the beneficial agent, wherein the clearance is a difference between an exterior diameter of the external ribs and an interior diameter of the capsule and wherein the external ribs are between about −1% and about 8% larger than an interior diameter of grooves in the capsule; and plugging an open end of the delivery device capsule with the selected membrane plug.

10. The method of forming a delivery device according to claim 9, wherein the clearance is a difference between the core diameter of the membrane plug and an interior diameter of the capsule.

11. The method of forming a delivery device according to claim 10, wherein the core diameter of the membrane plug is between 0.5 and 15 percent, smaller than the interior diameter of the capsule.

12. The method of forming a delivery device according to claim 9, wherein the clearance is determined by a height of the ribs in a direction parallel to a longitudinal axis of the delivery device.

13. The method of forming a delivery device according to claim 9, wherein the membrane plug is selected from a plurality of plugs having rib diameters which are the same and having different core diameters.

14. A method of making an osmotic delivery device for delivery of beneficial agents comprising:

filling a reservoir in a delivery device body with a beneficial agent and an osmotic agent;

providing a membrane plug for sealing an opening in the body, the membrane plug formed of a material which allows aqueous fluid to pass through the membrane into the osmotic agent and prevents the osmotic agent from passing out of the body; and compensating for variations in raw materials used for the membrane plug by changing a clearance between the membrane plug and an interior of the body, wherein compensation for variations in the raw materials is performed by selecting a membrane plug having a core diameter between a plurality of ribs which is between 0.5 and 15 percent smaller than an interior diameter of the body.

15. The method of making an osmotic delivery device according to claim 14, wherein a piston is positioned in the body between the beneficial agent and the osmotic agent.

16. A method of controlling a release rate of an osmotic delivery device for delivery of beneficial agents comprising:

providing a delivery device body with a reservoir containing a beneficial agent, a beneficial agent delivery outlet through which the beneficial agent is released, an osmotic agent, and a membrane plug positioned between the osmotic agent and an exterior of the body, the membrane plug allowing aqueous fluid to pass into the reservoir to swell the osmotic agent while preventing fluid from passing out of the body through the membrane plug, the membrane plug having a diameter which fits into an end of the reservoir; and controlling the release rate of the beneficial agent from the body by selecting a clearance between the membrane plug and an interior of the body such that a release rate of a delivery device with a smaller clearance is lower than a release rate of a delivery device with a larger clearance, wherein the clearance is selected such that external ribs of the membrane plug are between about −1% and about 8% larger than an interior diameter of groves in the device body.

\* \* \* \* \*

UNITED STATES PATENT AND TRADEMARK OFFICE
CERTIFICATE OF CORRECTION

PATENT NO.   : 6,113,938
DATED        : September 5, 2000
INVENTOR(S)  : Guohua Chen, et al.

It is certified that error appears in the above-identified patent and that said Letters Patent is hereby corrected as shown below:

Column 13,
Line 44, replace "is between 0.5 and 15 percent, smaller than the interior" with -- is between 0.5 and 15 percent smaller than the interior --.

Column 14,
Line 47, replace "groves" in the device body." with -- grooves in the device body. --

Signed and Sealed this

Thirtieth Day of October, 2001

Attest:

*Nicholas P. Godici*

NICHOLAS P. GODICI
*Attesting Officer*      *Acting Director of the United States Patent and Trademark Office*